(12) United States Patent
Talapov et al.

(10) Patent No.: US 7,450,783 B2
(45) Date of Patent: Nov. 11, 2008

(54) METHODS AND SYSTEMS FOR MEASURING THE SIZE AND VOLUME OF FEATURES ON LIVE TISSUES

(75) Inventors: Andrei L. Talapov, Germantown, MD (US); Ibrahim Cem Girit, Plainsboro, NJ (US)

(73) Assignee: Biopticon Corporation, Plainsboro, NJ (US)

( * ) Notice: Subject to any disclaimer, the term of this patent is extended or adjusted under 35 U.S.C. 154(b) by 714 days.

(21) Appl. No.: 10/931,661

(22) Filed: Sep. 1, 2004

(65) Prior Publication Data
US 2005/0084176 A1  Apr. 21, 2005

Related U.S. Application Data

(60) Provisional application No. 60/502,364, filed on Sep. 12, 2003.

(51) Int. Cl.
*G06K 9/36* (2006.01)
*G06K 9/00* (2006.01)

(52) U.S. Cl. .................. 382/286; 382/128; 382/154; 382/131; 382/133; 600/411; 600/372; 600/122; 600/407; 600/475; 128/923; 128/899; 128/916

(58) Field of Classification Search .............. 382/154, 382/128, 286, 133, 224, 132, 131, 100; 128/923, 128/899, 916; 600/411, 372–374, 407, 424, 600/122, 475; 378/37
See application file for complete search history.

(56) References Cited

U.S. PATENT DOCUMENTS

| | | | | |
|---|---|---|---|---|
| 4,515,165 A | * | 5/1985 | Carroll | 600/475 |
| 4,839,807 A | * | 6/1989 | Doi et al. | 382/128 |
| 4,851,984 A | * | 7/1989 | Doi et al. | 382/108 |
| 5,810,014 A | * | 9/1998 | Davis et al. | 600/508 |
| 5,921,937 A | * | 7/1999 | Davis et al. | 600/508 |
| 6,278,793 B1 | * | 8/2001 | Gur et al. | 382/128 |
| 6,879,394 B2 | | 4/2005 | Amblard et al. | |
| 7,103,205 B2 | * | 9/2006 | Wang et al. | 382/132 |

(Continued)

FOREIGN PATENT DOCUMENTS

EP  0 552 526 B1  10/1997

(Continued)

OTHER PUBLICATIONS

International Search Report and Written Opinion for International Application No. PCT/US2004/028445 filed Sep. 1, 2004.

(Continued)

*Primary Examiner*—Samir A Ahmed
*Assistant Examiner*—Nancy Bitar
(74) *Attorney, Agent, or Firm*—Wilmer Cutler Pickering Hale and Dorr LLP

(57) ABSTRACT

Methods and systems for measuring volume and size of features such as lesions, tumors, sores, and wounds external to animal, human and plant skin, using 3D structured light scanners are provided. These methods and systems obtain a point cloud of the scanned feature, and employ algorithms to adjust the suggested feature geometry parameters to minimize deviations of the point cloud from suggested feature geometry. Obtained geometry parameters permit the calculation of the features' sizes and volumes.

16 Claims, 5 Drawing Sheets

U.S. PATENT DOCUMENTS

2005/0111757 A1*  5/2005  Brackett et al. ............. 382/294
2007/0065009 A1*  3/2007  Ni et al. ..................... 382/173

FOREIGN PATENT DOCUMENTS

WO      WO 00/03210         1/2000

OTHER PUBLICATIONS

Lewis JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.

Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the tissue, Proc. SPIE, vol. 4952, 39 (2003), DOI:10.1117/12.474081, Online Publication Date: Jul. 28, 2003.

* cited by examiner

METHODS AND SYSTEMS FOR MEASURING THE SIZE AND VOLUME OF FEATURES ON LIVE TISSUES

CROSS REFERENCE TO RELATED APPLICATION

This application claims the benefit under 35 U.S.C. § 119(e) of U.S. Provisional Patent Application No. 60/502,364, filed Sep. 12, 2003, which is hereby incorporated by reference herein in its entirety.

FIELD OF THE INVENTION

This invention relates generally to the field of measurement of size and volume, and, in particular, to the measurement of size and volume of features such as tumors, lesions, sores, wounds on the surface of animals, plants and humans using 3D image construction from 2D images of the object and patterned light superimposed over the object.

BACKGROUND

The identification and selection of potentially active drugs for use in treatment of diseases, (for example, cancer) has largely been based on the screening of large numbers of compounds and rational drug design (when the molecular structure of the target such as tumor is known). Once compounds have been chosen based on selectivity to the target and desired functional effect, the ultimate test for advancement of a compound to clinical testing is to show its safety and its efficacy in multiple animal models.

There are several current methods and devices that are used to assess the growth of abnormal external features such as tumors, lesions, sores, port stains and wounds in such animal models. The simplest is to measure a feature in two dimensions, length and width, with the aid of a mechanical or electronic caliper that is manually operated. An approximate volume formula is then used to calculate the area or the volume of the object by assuming an ellipsoid shape of the mass. This is the most commonly used method, since it is simple and the calipers cost very little.

Unfortunately, this approach has obvious pitfalls related to the instrument and methodology used to calculate volume as well as operator-related errors. First, a major source of inaccuracy or variability is caused by the operator's judgment on the choice of the ellipsoid axes. For example, in making a measurement, a different operator may select a different choice of ellipsoid axes. Second, this approach is fairly time consuming. In the case of cancer studies, for example, a single study may involve hundreds of animals, and because the tumor volume measurements have to be done at least twice a week and take a given amount of investigator time per measurement, there is a limit in the number of studies that a single investigator can handle at once. Therefore, a different approach is needed to eliminate the inaccuracies of the methodology and instrumentation used and the subjectivity introduced by the operator.

Other mechanical volume measuring devices come closer to being an automated volume measurement system. These mechanical devices include a cylindrical chamber filled with elongated pins or filaments which, when pressed over a tumor or any other mass, convert the shape of the mass into volume information. Such devices require direct contact to features such as tumors, however.

The most sophisticated methods for measuring a mass include Computer Aided Tomography (CAT) using X-rays, Magnetic Resonance Imaging (MRI) using magnetic scans, Positron Emission Tomography (PET) using electrons and Single Photon Emission Computer Tomography (SPECT) using gamma rays. Such methods are capable of obtaining more accurate size and volume information about both external and internal features such as tumors and organs. The use of such methods is not feasible in many cases, however, due to long and costly preparation times, the unwanted effects of the contrast agents and radioactive compounds and the necessity to anesthetize animals during measurement.

Notwithstanding the availability of the foregoing techniques, there is no method or device for non-contact and fast measurement of the volume of surface features of small animals that can be used in, for example, pre-clinical cancer and inflammation studies. All the methods discussed above suffer from a number of disadvantages. For example, manual caliper measurements are prone to significant subjective operator errors; CAT, PET, MRI and SPECT methods are unacceptably time consuming and expensive; and caliper and cylindrical chamber methods require direct contact with the object under measurement, which is a potential source of feature deformation and contamination that may negatively effect the measurements being made.

As a result there is a need for methods and systems that accurately and quickly measure the volume/size of surface features such as wounds on the surface of animals, plants and humans.

SUMMARY OF INVENTION

The methods and systems of the present invention utilize a 3D structured light scanner and geometry based feature recognition logic to obtain shape, size and/or volume of the animal surface features observed in clinical studies. Such features may include tumors, lesions, sores, and wounds and any other suitable feature on the surface of animals, plants and humans, and any other suitable surface. The invention may obtain a number of 2D images of the surface feature, such as a tumor, with patterns of structured light projected on the feature. The parallax between a camera and a light source is used to compute a 3D point cloud of the feature's surface. The point cloud is a collection of (x, y, z) coordinates of the surface feature points. Recognition algorithm separates the feature points from the healthy points by minimizing the standard deviation of the point cloud points from the suggested shape. After the separation is achieved, the feature size and volume may be calculated.

In one embodiment, a system in accordance with the invention includes a 3D structured light scanner, controlled by a processor. The scanner obtains a set of 2D images of structured light, projected to the scanned object, and, in some implementations, extracts the structured light coordinates from these images. The processor obtains the images and/or structured light coordinates from the scanner. Using this data, the processor calculates the point cloud, separates the feature shape, finds its sizes and/or volume, and records the results in a measurement database In this way, the invention provides for fast, non-contact, automated measurements of external features such as tumors, lesions, sores, wounds shape, size and volume on the surface of animals, plants and humans.

The invention also provides time savings, which are extremely important when measuring, for example, tumor progress using large animal sets. For example, the 3D scanner of the present invention is many times faster than CAT methods. Compared to caliper method, the 3D scanner measurements are also faster. In addition, the 3D scanner method may be completely automated (i.e., measurement data may be electronically transferred to a computer from a measuring device, eliminating extra time needed to record and transfer paper recorded data to computers).

The invention may further be totally non-invasive (i.e., no part of the device touches the animal). This leads to three important consequences, for example, for making tumor volume measurements: i) animals are not stressed as much, which less affects the tumor growth; ii) there is no need to sterilize the device; and iii) tumors are not deformed by the measuring equipment. Only the 3D scanner light touches the animals. The 3D scanner method does not involve injecting contrast agents or radioactive substances into animals. Since it takes a very short time, around a few seconds, to complete the measurement, the 3D scanner method is less stressful to animals and preferably does not require anesthetizing them.

Thus, in accordance with certain embodiments of the invention, methods and systems for measuring characteristics of a feature portion on the surface of living tissue also having a non-feature portion are provided. These methods and systems obtain a set of 3-dimensional coordinates corresponding to points on the surface of the living tissue using a 3-dimensional scanner, separate a feature portion of the set, which corresponds to the feature portion of the surface, from a non-feature portion of the set, which corresponds to the non-feature portion of the surface, and calculate the size of the feature based on the feature portion of the set.

Further in accordance with the invention, certain embodiments also include: basing the separation and calculation upon the feature portion of the surface having a predetermined feature shape and the non-feature portion of the surface having predetermined non-feature shape; the: predetermined feature shape and the predetermined non-feature shape being described by a finite set of parameters; performing successive approximations to find the set of parameters; selecting an arbitrary initial choice of the set of parameters for the successive approximations; calculating distances between coordinates in the set and each of the predetermined feature shape and the predetermined non-feature shape; assigning the coordinates in the set to the feature portion of the set when the coordinates are closer to the predetermined feature shape than to the predetermined non-feature shape, and to the non-feature portion of the set when the coordinates are closer to the predetermined non-feature shape than to the predetermined feature shape; finding the set of parameters by minimizing the standard deviation of the feature portion of the set from the predetermined feature shape and by minimizing the standard deviation of the non-feature portion of the set from the predetermined non-feature shape; and calculating the size of the predetermined feature shape based on the set of parameters and estimating the size of the feature portion of the surface to be the size of the predetermined feature shape.

BRIEF DESCRIPTION OF THE DRAWINGS

The preferred embodiments of the invention are described below in connection with the accompanying drawings, in which like reference numerals refer to like parts throughout and in which.

DETAILED DESCRIPTION OF THE PREFERRED EMBODIMENTS

In the following detailed description, numerous specific details are set forth regarding the methods and systems of the present invention and the environments in which the methods and systems may operate in order to provide a thorough understanding of the present invention. It will be apparent to one skilled in the art, however, that the present invention may be practiced without such specific details. In other instances, well-known components, structures and techniques have not been shown in detail to avoid unnecessarily obscuring the subject matter of the present invention. Moreover, various examples are provided to explain the operation of the present invention. It should be understood that these examples are merely illustrative and various modifications may be made in accordance with the invention. It is contemplated that there are other methods and systems that are within the scope of the present invention.

Many designs of the 3D structured light scanners are known, and some of them are available commercially. While many 3D scanner capable of providing point cloud that is the collection of (x, y, z) coordinates of the surface feature points, may be used by the methods and systems of the present invention, not all known designs provide combination of accuracy and speed, suitable for scanning of live animal surface features. For this reason, different illustrative embodiments of a 3D scanner of the present invention are described below.

Both illustrative embodiments use the scanning by one moving stripe of light, projected on the scanned object. The motion of the stripe is synchronized with the video stream of stripe images on the scanned object.

Each video field of this video stream captures one stripe image position. These images are used either by a customized video Digital Signal Processor DSP, or by PC based software to extract the $(x_p, y_p)$ pixel coordinates of the stripe in the images. These $(x_p, y_p)$ pixel coordinates, together with the video field number N, identify the stripe point in 3-dimensional parameter space $(x_p, y_p, N)$. A PC software program is used, as described later, to convert from this parameter space to $(x_o, y_o, z_o)$ coordinates of the object points in the real world.

Figure 1:
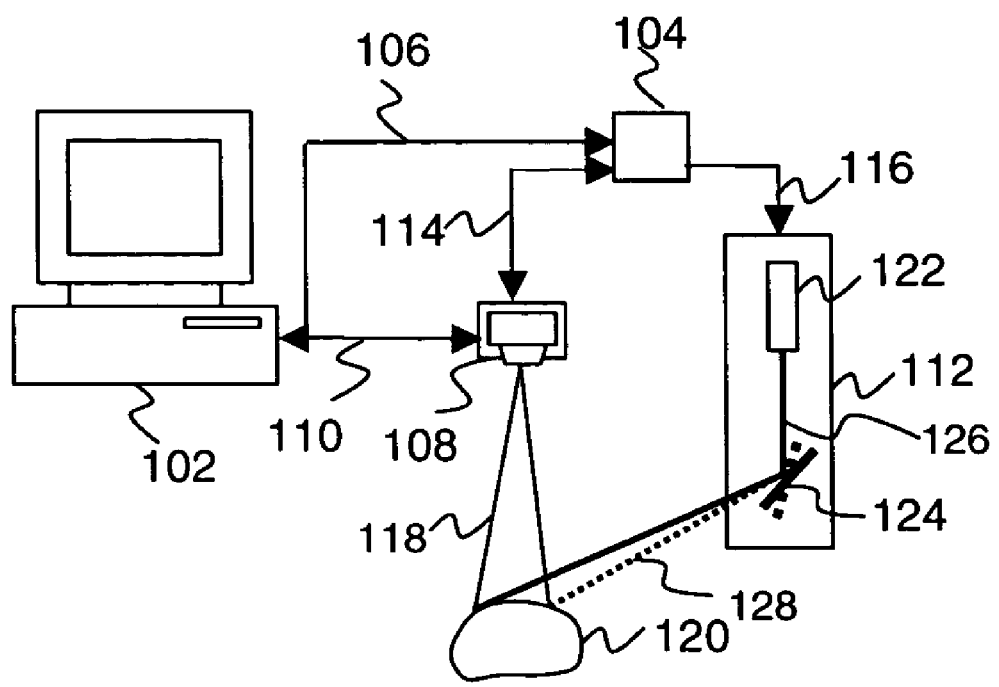
FIG. 1 is a block diagram of a system using a Personal Computer (PC) for image processing in accordance with certain embodiments of the present invention.

Turning to FIG. 1, a system 100 in accordance with one embodiment of the invention is shown. As illustrated, system 100 may include a PC 102, a microcontroller 104, a data link 106, a camera 108, a camera link 110, a stripe positioning system 112, a control link 114, and a control link 116. The scanner operation is controlled by the PC 102. The PC may be any suitable hardware and/or software for controlling system 100, such as a personal computer, a processor, dedicated logic, etc. The PC is connected to microcontroller 104 using data link 106. Microcontroller 104 may be any suitable hardware for controlling stripe positioning system 112 and/or camera 108, and maybe incorporated for hardware and/or software in PC 102. When running a non-real-time operating system, a separate microcontroller may be necessary. Link 106 may be a USB connection, an IEEE 1394 connection, or any other suitable connection that is used to send commands to set the scan parameters, to start the scan, to get the information that the scan is completed and for any other suitable purpose. The PC 102 also connected to the video camera 108 by the camera link 110. Camera 108 may be any suitable device for capturing a light stripe 118 image on the scanned object and may be connected to microcontroller 104 by control link 114. Control link 114 may be any suitable control link for controlling camera 108. Camera link 110 may be an analog or digital link such as a USB connection, an IEEE 1394 connection, a Camera Link connection, or any other suitable connection. Link 110 may be used to transfer a video signal from camera 108 to PC 102. When this signal is an analog signal, suitable circuitry in PC 102, such as a frame grabber, may be used to digitize the signal for processing. The video signal contains information about the stripe light 118, on the scanned object 120. This information may be used to find a surface point cloud corresponding to the surface of scanned object 120, as explained below. The video signal may also used for a video preview of subsequent scanning.

As also shown in FIG. 1, stripe positioning system 112 may include a source 122 and a controllable mirror 124. Source 122 may be any suitable source of a detectable stripe 126, such as a laser, a focused non-laser light source, or other form of suitable energy, etc. Mirror 124 may be any mechanism suitable for positioning stripe 128. Source 122 and mirror 124 may be controlled via control link 116, which may be any suitable link for controlling source 122 and mirror 124. The light that is reflected off object 120 forms reflected light 118.

Figure 2:
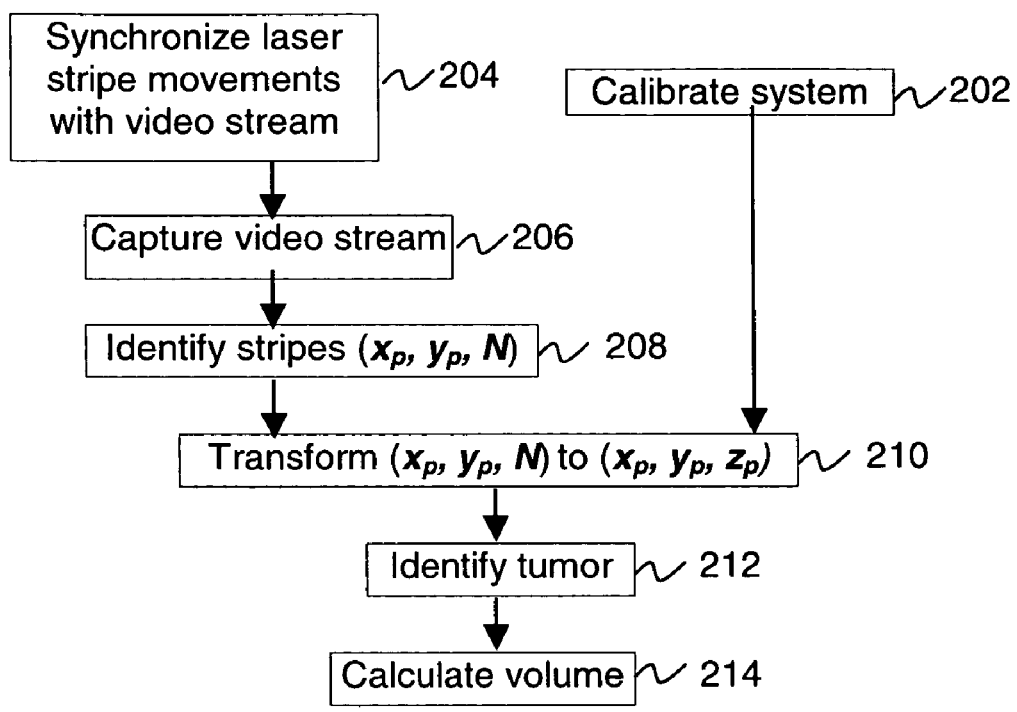
FIG. 2 is a flow chart of a process using a PC for image processing in accordance with certain embodiments of the present invention.

A process 200 for operating system 100 is shown in FIG. 2. As illustrated, before any feature scans are performed, at step 202, video camera 108 and stripe positioning system 112 are calibrated by extracting information from video images of a stripe 128, taken at different positions on objects of known shape and size. In step 204 and 206, microcontroller 104, synchronizes the light 126 and the mirror 124 movements with the video camera 108 field sync signals through the control link 114. Microcontroller 104 controls mirror 124 through an electronic link 116 so that stripe 126 takes different positions on object 120, while camera 108 takes images of the stripe at these positions as part of a video sequence. At step 206, the video sequence, consisting of several video frames, is captured by using the data video link 110. Each video field has an image of one stripe position at different location. At step 208, pixel coordinates $(x_p, y_p)$ of the stripe 128 image are extracted from the video data, and the stripe line number N is assigned according to the field number after the camera sync. At step 210, the $(x_p, y_p, N)$ array, and the calibration data, obtained earlier at step 202, are used to calculate scanned object point cloud, as described below. Feature shape identification in step 212 is also described below. After the feature is identified, the volume calculation 214 is done as described below.

Figure 3:
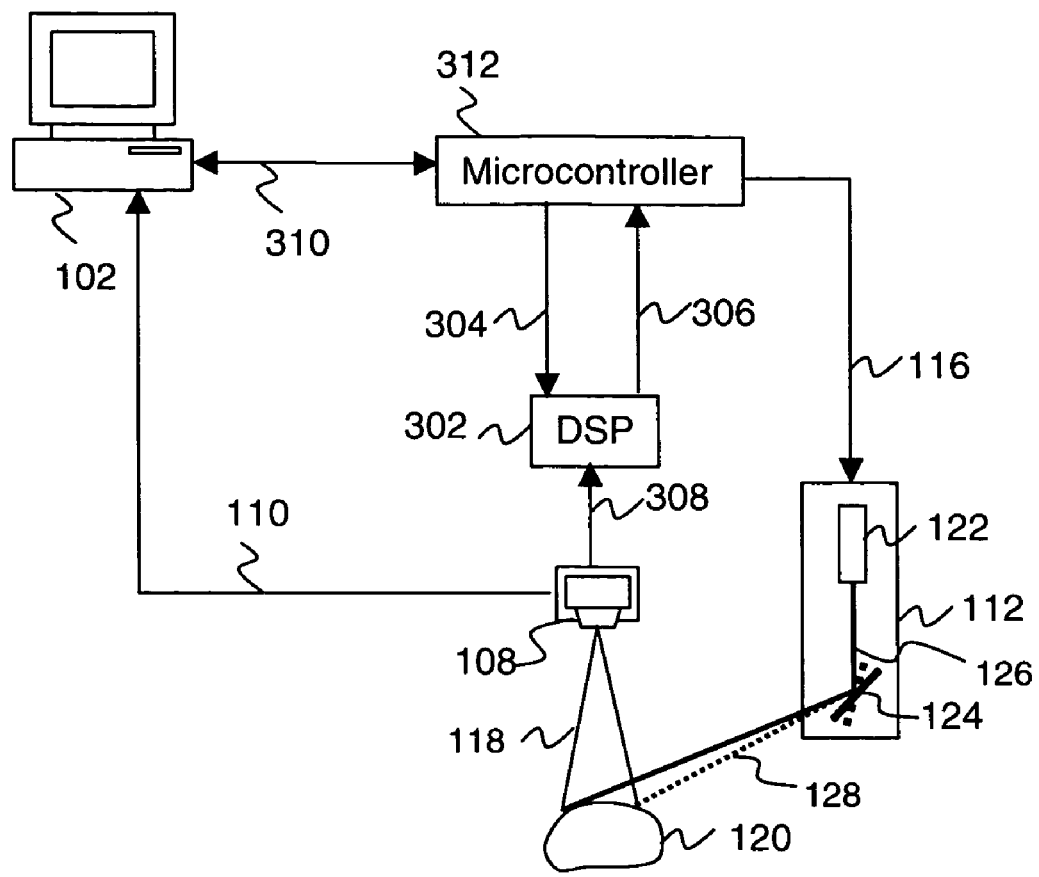
FIG. 3 is a block diagram of another system using a DSP for image processing in accordance with certain embodiments of the present invention.

Turning to FIG. 3, an alternate form of the embodiment of the invention in FIG. 1 is shown as system 300. Except as set forth below, system 300 is substantially identical to system 100. However, as illustrated, unlike system 100, system 300 includes a DSP 302 connected between camera 108 and microcontroller 312 by links 304, 306, and 308. As in the previous implementation, the scanner operation is controlled by the PC 102. The PC is connected to microcontroller 302 using the data link 310, which may be USB or IEEE 1394 cable. This link 310 is used to send commands to set the scan parameters, to start the scan, and to get the information that the scan is completed. It is also used to read the scan data from the DSP 302 output memory. The PC 102 also connected to the video camera 108 by the video link 110, which may be analog cable carrying analog video signal to be digitized by the frame grabber inside the PC. It also may be digital link, such as USB, IEEE 1394, or Camera Link. In any case, this link 110 is used to get the video signal form the camera into PC. Unlike in the previous implementation, this video signal is not used to extract the geometry information from the video stream. Instead, it is used for the video preview and, possibly, for color still image, which may be necessary for documentation purposes.

The stripe light 118, reflected from the scanned object 120, carries information about the scanned object geometry. The video signal of this light is captured by the video camera 108. The output signal 308 of this camera may be analog signal. In such a case it is digitized inside the DSP 302. It also may be digital signal, supplied immediately to the logic part of the DSP 302.

Figure 4:
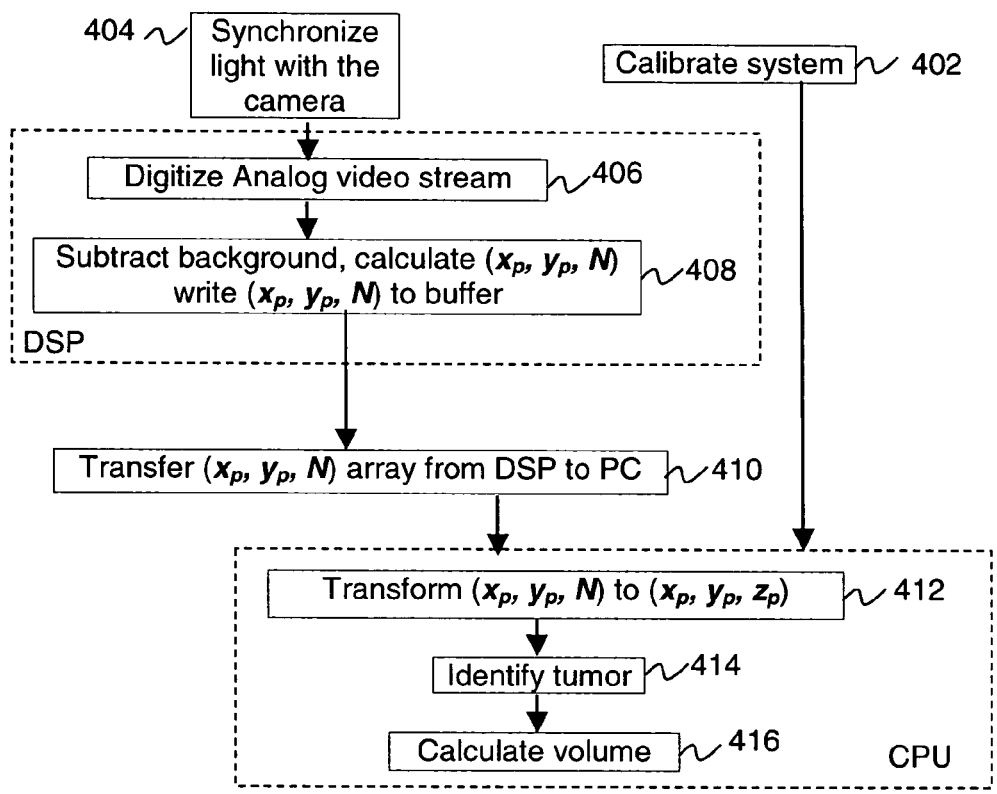
FIG. 4 is a flow chart of another process using a DSP for image processing in accordance with certain embodiments of the present invention.

Turning to FIG. 4, a process 400 for operating system 300 is shown. Beginning at step 402, long before any feature scans are performed, the video camera 108 and the light positioning system 112 are calibrated by obtaining $(x_p, y_p, N)$ arrays by the DSP from the scans of the objects of exactly known shape and size. At step 404, a microcontroller 312, programmable by PC 102, synchronizes the light 120 provided by a light source 122 and the mirror 124 movement with the video camera field sync signals in the video signal on link 308. The communication between microcontroller 300 and the light positioning system 112 is established through an electronic link 116. In step 406, an analog camera output is captured by a digitizer which is part of DSP chip 302, and fed to DSP 302, logic part of which may be implemented in a FPGA. Obviously, when camera 108 outputs to DSP 302 a digital signal instead of an analog signal, step 406 may be omitted. At step 408, DSP 302 does background subtraction by subtracting the video fields obtained with structured light off from the fields with structured light on. The subtraction operation is done by using the background memory, which is part of the DSP 302. Also in step 408, the pixel coordinates $(x_p, y_p)$ of all stripe points are found, the stripe number N is assigned to each point, and the array $(x_p, y_p, N)$ are written to an output buffer. In step 410, the microcontroller 300 reads the $(x_p, y_p, N)$ from the DSP output buffer through an electronic data bus 110, and sends it to the host PC. Microcontroller 300 controls DSP 302 through a bus 304 to send necessary commands and processing parameters. Further processing is done by the host PC. So, the steps 412, 414 and 416 are the same as steps 210, 212 and 214 of the previous implementation.

Step 412 which is substantially identical to step 210 is performed next. At this step, the processes convert coordinates $(x_p, y_p, N)$ into real 3-dimensional object coordinates $(x_o, y_o, z_o)$. This step is performed using a mathematical model of the 3D scanner, which consists of the camera model, and the model describing positions of the light plane relative to the camera 108.

Figure 5:
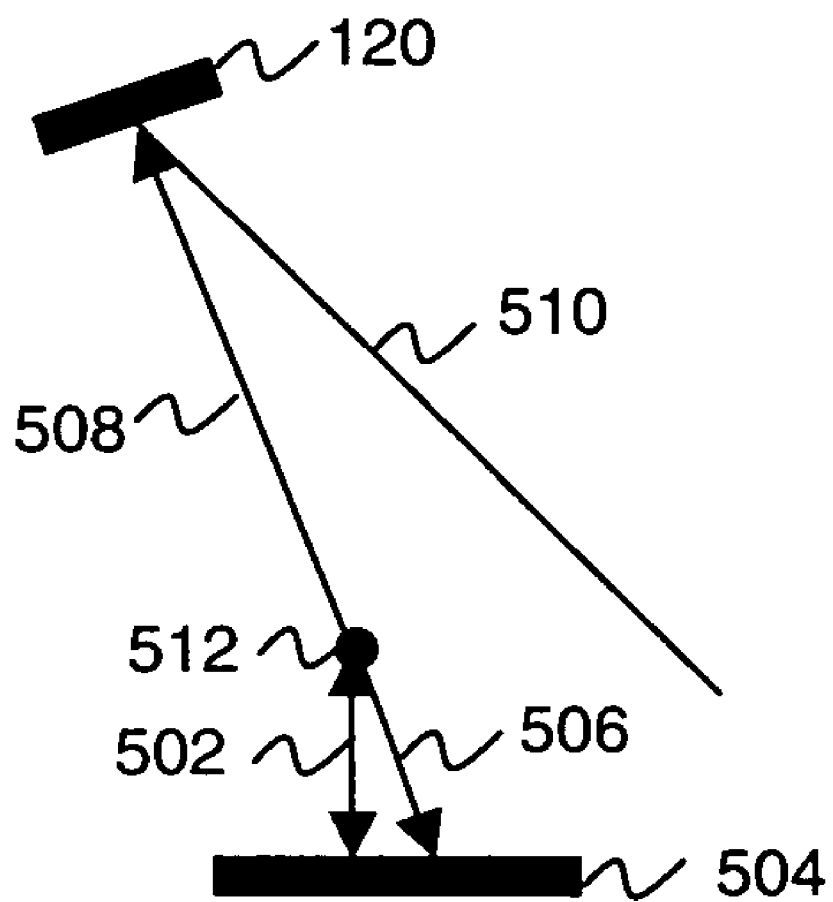
FIG. 5 illustrates a mathematical model of a 3D scanner in accordance with certain embodiments of the present invention.

FIG. 5 illustrates a scanner model 500. As shown, in standard pinhole camera model, the camera lens is replaced by a pinhole 512, located at a focal distance length f 502 from the image plane 504 defined by a Charged Coupled Device CCD, in camera 108. The stripe image coordinates $(x_p, y_p)$ refer to this plane. If the beginning of the 3D coordinate system is placed at the pin hole 512, then the stripe image point position vector $\vec{r}_p$ 506 is equal to "$-(f, x_p, y_p)$".

As can be seen from FIG. 5, the CCD image point $\vec{r}_p$ 506 and the object point $\vec{r}_o$ 508 lie on the same line, which passes through the pinhole 512. This co-linearity is described as $\vec{r}_o = \eta \cdot \vec{r}_p$, where $\eta$ is a scalar coefficient. To find $\eta$, one more condition is needed. It is provided by the observation that the object point is also the light plane point. The light plane 510 is described by the equation $\vec{r}_{light\_plane} \cdot \vec{n}_{light\_plane} = 1$. So, for the point of the object intersection with light plane we have $\eta = 1/(\vec{r}_p \cdot \vec{n}_{light\_plane})$. Thus, the object $(x_o, y_o, z_o)$ vector is given by the following equation $$\vec{r}_0 = \frac{\vec{r}_p}{\vec{r}_p \cdot \vec{n}_{light\_plane}}$$

This formula may be used to calculate object coordinates in steps 210 or 410. The parameters $\vec{n}_{light\_plane}$ plane for each light plane, as well as the focal length f, are found by calibration during the step 202 or 402.

The calibration steps 202 or 402 are also used to find lens distortions. Standard axial symmetric lenses have distortions proportional to the square of distance of the image point from the optical axis. The coefficients of proportionality, found as a result of calibration, provide the necessary corrections to the above formulae, based on the pinhole model.

It should be emphasized here that the calculations according to the formulae above are necessary only in certain embodiments, where custom 3D stripe scanners are used. In general, any 3D scanner, including those that are commercially available, may be used to get the scanned object point cloud in accordance with the invention.

Next at steps 212 and 412, the feature points are separated from the healthy skin points in the point cloud provided by the 3D scanner. This is in essence a further explanation step 212 or 414 of the method described in FIGS. 2 and 4. For purposes of this explanation, it is assumed that the feature (such as tumor bump on the healthy skin) can be reasonably described by a limited number of parameters. In accordance with the invention, the standard deviation of the point cloud points from the assumed shape is minimized by adjusting these shape defining parameters.

For example, a feature (such as tumor) may be modeled as part of an ellipsoid cut off by a plane. The plane simulates healthy skin surface. The feature volume may be calculated as the volume of the part of the ellipsoid that is cut off by this plane. The calculation of the volume of the ellipsoid may be made by defining the parameters such as plane's position and the ellipsoid's position and orientation.

The healthy skin plane, as any plane, can be described by the following formula $\vec{n} \cdot \vec{r} = 1$, where $\vec{r} = (x, y, z)$ is the position of a point on the plane, and $\vec{n} = (n_x, n_y, n_z)$ is vector of a set of parameters describing the plane.

The scanner gives us a set of points $\vec{r}_i$, where i is the index of the scan point. If an ideal plane is available, just three points would have been sufficient to define the position of the plane. Unfortunately, the coordinate set, provided by the scanner, represents the healthy feature skin, and this is not an ideal plane. So the best possible approximation of the healthy feature skin by a plane is used. The reasonable approach is to look for the plane which provides least possible standard deviation of the healthy feature skin points from this plane. More accurately, the distance between the plane and the point $\vec{r}_i$ is given by the formula $$\frac{|\vec{n} \cdot \vec{r}_i - 1|}{|\vec{n}|}.$$

To find the plane position $\vec{n}$, the sum of squares of such distances for all the points, which should be approximated by the plane, is minimized. In other words, the expression $$\sum_i \frac{(n_x \cdot x_i + n_y \cdot y_i + n_z \cdot z_i - 1)^2}{(n_x^2 + n_y^2 + n_z^2)}$$

is minimized as a function of three variables $n_x$, $n_y$, and $n_z$. The problem then is reduced to a nonlinear minimization problem which can be solved by standard methods.

There is still a need to distinguish between the points belonging to the healthy skin, whose coordinates should be included into the sum, and the feature such as tumor points, whose coordinates should be included in the ellipsoid parameter calculations, and therefore should not be included in the plane parameter calculations. Before describing the method to do that, a method to find ellipsoid parameters should be considered.

For the sake of simplicity, consider first the simplest version of an ellipsoid: a sphere. A sphere is defined by four parameters: the three coordinates of the sphere center $\vec{r}_{center} = (x_{center}, y_{center}, z_{center})$, and the sphere radius R. The distance between the approximating sphere surface and the scanner-provided point $\vec{r}_i$ is given by the formula $\|\vec{r}_i - \vec{r}_{center}\| - R|$.

To find the sphere parameters, the sum of squares of such distances for all the points, which should be approximated by the sphere, is minimized. In other words, the following sum $$\sum_i \left( \sqrt{(x_i - x_{center})^2 + (y_i - y_{center})^2 + (z_i - z_{center})^2} - R \right)^2$$

is minimized as a function of $(x_{center}, y_{center}, z_{center})$ and R. This nonlinear minimization problem is treated the same way as the problem of finding plane parameters.

For an ellipsoid, the square of the distance between the scanner-provided point $\vec{r}_i$ and the ellipsoid surface is equal to $(x_i - x_{ell})^2 + (y_i - y_{ell})^2 + (z_i - z_{ell})^2$. Here $(x_{ell}, y_{ell}, z_{ell})$ are the coordinates of the point on the ellipsoid, closest to the scanner-provided point $\vec{r}_i$. To find this ellipsoid point, it is convenient to use the new coordinate system, related to the main axes of the ellipsoid. The transformation to such coordinate system is achieved by one translation and one rotation in the 3-dimensional space. The translation and rotation parameters should be regarded as the parameters to be found as a result of minimization, as described below.

In the coordinate system, defined by the main axes of the ellipsoid, coordinates of any point of the ellipsoid surface satisfy the equation $$\frac{x_{ell}^2}{a^2} + \frac{y_{ell}^2}{b^2} + \frac{z_{ell}^2}{c^2} = 1,$$

where a, b, and c define ellipsoid sizes. The normal vector to the ellipsoid surface is proportional to gradient of the ellipsoid equation, which is given by the vector $$\left[\frac{x_{ell}}{a^2}, \frac{y_{ell}}{b^2}, \frac{z_{ell}}{c^2}\right].$$

The vector between the scanner-provided point $\vec{r}_i$ and the closest ellipsoid point should be proportional to the normal vector. That means the following equation should be satisfied:

$$((x_i - x_{ell}), (y_i - y_{ell}), (z_i - z_{ell})) = \lambda_i \left[\frac{x_{ell}}{a^2}, \frac{y_{ell}}{b^2}, \frac{z_{ell}}{c^2}\right]$$

where $\lambda_i$ is some scalar coefficient. This equation can be used to express $(x_{ell}, y_{ell}, z_{ell})$ as functions of $\lambda_i$ and of coordinates of scanner-provided point $\vec{r}_i$. These expressions may be put back to the equation of the ellipsoid, giving the following equation for the $\lambda_i$:

$$x_i^2 \cdot \left[\frac{a}{\lambda_i + a^2}\right]^2 + y_i^2 \cdot \left[\frac{b}{\lambda_i + b^2}\right]^2 + z_i^2 \cdot \left[\frac{c}{\lambda_i + c^2}\right]^2 = 1$$

After $\lambda_i$ is found as solution of this equation, it should be used to calculate the distance between the scanner-provided point $\vec{r}_i$ and the ellipsoid. The minimization should include sum of squares of such distances for all scan points assigned to the ellipsoid:

$$\sum_i \lambda_i^2 \cdot \left[\left[\frac{x_i}{\lambda_i + a^2}\right]^2 + \left[\frac{y_i}{\lambda_i + b^2}\right]^2 + \left[\frac{z_i}{\lambda_i + c^2}\right]^2\right]$$

To distinguish the healthy skin plane points from feature ellipsoid points, an optimization in the space of the plane and ellipsoid parameters is used: First, some initial set of the plane and the ellipsoid parameters is chosen. Using these parameters, the distance between any point and the plane and between the same point and ellipsoid can be calculated. Accordingly, the scan points, which are closer to the plane, are assigned to the plane, and the rest are assigned to the ellipsoid. Then the standard deviation for the complete point cloud is calculated. This standard deviation, as a function of the plane and ellipsoid parameters is the target function to be minimized. Standard nonlinear minimization methods, such as described in the book Numerical Recipes in C, Cambridge University Press, ISBN 0521 43108 5, Chapter 10.5 Direction Set (Powell's) Methods in Multidimensions, pp 412-420, which is hereby incorporated by reference herein in its entirety, can be used to find the minimum.

The set of parameters, providing the minimum, gives the plane position and the ellipsoid shape, sizes, and position relative to the plane. Having these parameters, the feature size or volume is calculated in step 214 or 416 as described below.

Volume Calculation:

Minimization provides the ellipsoid and the plane parameters. It is convenient to perform volume calculations in the ellipsoid-related coordinate system. In this coordinate system, the ellipsoid is described by the equation $$\frac{x_{ell}^2}{a^2} + \frac{y_{ell}^2}{b^2} + \frac{z_{ell}^2}{c^2} = 1,$$

and the plane is described by the equation $\vec{n} \cdot \vec{r} = 1$. Standard geometry calculations may be used to determine if there is an intersection between the ellipsoid and the plane. If there is no such intersection, then the feature (tumor) volume is given by the ellipsoid volume:

$$\frac{4}{3} \cdot \pi \cdot a \cdot b \cdot c$$

On the other hand, if there is the intersection between the ellipsoid and the plane, then the ellipsoid volume is divided into two parts, and only the volume of one of these parts is the volume of the feature. While the numerical volume calculation is trivial, the volume calculation formulae are complex. To avoid complicated formulae, we show only the analytic result for the case when the feature is represented by a small part of the ellipsoid that is cut off by the plane, and the plane is orthogonal to one of the main axes of the ellipsoid. If the z-axis is chosen as such axis, then the plane equation can be written as $h \cdot z = 1$. For this case the feature volume is equal to $$\pi \cdot a \cdot b \cdot c \cdot \left(\Delta^2 - \frac{\Delta^3}{3}\right) \text{ where}$$

$$\Delta = 1 - \frac{h}{c}.$$

Although the invention has been described and illustrated in the foregoing illustrative embodiments, it should be understood that the present disclosure has been made only by way of example, and that numerous changes in the details of construction and combination and arrangement of processes and equipment may be made without departing from the spirit and scope of the invention.

What is claimed is:

1. A method for measuring characteristics of a feature portion on the surface of living tissue also having a non-feature portion, comprising:

obtaining a set of 3-dimensional coordinates corresponding to points on the surface of the living tissue using a 3-dimensional structured light scanner;

calculating distances between the coordinates in the set and each of coordinates of a predetermined feature shape and coordinates of a predetermined non-feature shape;

assigning the coordinates in the set to a feature portion of the set, which corresponds to the feature portion of the surface, when the coordinates are closer to the coordinates of the predetermined feature shape than to the predetermined non-feature shape;

assigning the coordinates in the set to a non-feature portion of the set, which corresponds to the non-feature portion of the surface, when the coordinates are closer to the coordinates of the predetermined non-feature shape than to the predetermined feature shape; and calculating the size of the feature based at least in part on an intersection of the feature portion of the set and the non feature portion of the set.

2. The method according to claim 1, wherein the predetermined feature shape and the predetermined non-feature shape are described by a finite set of parameters.

3. The method according to claim 2, further comprising performing successive approximations to find the set of parameters.

4. The method according to claim 3, further comprising selecting an arbitrary initial choice of the set of parameters for the successive approximations.

5. The method according to claim 2, further comprising finding the set of parameters by minimizing the standard deviation of the feature portion of the set from the predetermined feature shape and by minimizing the standard deviation of the non-feature portion of the set from the predetermined non-feature shape.

6. The method according to claim 5 wherein the calculating the size comprises calculating the size of the predetermined feature shape based on the set of parameters and estimating the size of the feature portion of the surface to be the size of the predetermined feature shape.

7. A system for measuring characteristics of a feature portion on the surface of living tissue also having a non-feature portion, comprising:
a 3-dimensional structured light scanner for obtaining a set of 3-dimensional coordinates corresponding to points on the surface of the living tissue;
and a processor that:
calculates distances between the coordinates in the set and each of coordinates of a predetermined feature shape and coordinates of predetermined non-feature shape;
assigns the coordinates in the set to a feature portion of the set, which corresponds to the feature portion of the surface, when the coordinates are closet to the coordinates of the predetermined feature shape than to the predetermined non-feature shape;
assigns the coordinates in the set to a non-feature portion of the set, which corresponds to the non-feature portion of the surface, when the coordinates are closer to the coordinates of the predetermined non-feature shape than the predetermined feature shape; and
calculates the size of the feature based at least in part on an intersection of the feature portion of the set and the non feature portion of the set.

8. The system according to claim 7, wherein the predetermined feature shape and the predetermined non-feature shape are described by a finite set of parameters.

9. The system according to claim 8, wherein the processor also performs successive approximations to find the set of parameters.

10. The system according to claim 9, wherein the processor selects an arbitrary initial choice of the set of parameters for the successive approximations.

11. The system according to claim 8, wherein the processor also finds the set of parameters by minimizing the standard deviation of the feature portion of the set from the predetermined feature safe and by minimizing the standard deviation of the non-feature portion of the set from the predetermined non-feature shape.

12. The system according to claim 11, wherein the processor, in calculating, calculates the size of the predetermined feature shape based on the set of parameters and estimates the size of the feature portion of the surface to be the size of the predetermined feature shape.

13. The method of claim 1, wherein the predetermined feature shape is an ellipsoid and the predetermined non-feature shape is a plane.

14. The method according to claim 1, further comprising:
projecting, from a light source, a stripe of light comprising points of light separated by known distances across the surface of the living tissue substantially in a first dimension;
moving the stripe of light across the surface of the living tissue substantially in a second dimension;
capturing images of the stripe of light at intervals synchronized with the moving of the stripe of light, using a camera; and
obtaining the set of 3-dimensional coordinates based at least in part on, the known distances, capturing images of the stripe of light at intervals synchronized with the moving of the stripe of light, and parallax between the camera and the light source.

15. The system according to claim 7, wherein the predetermined feature shape is an ellipsoid and the predetermined non-feature shape is a plane.

16. The system according to claim 7, further comprising:
a light source that projects a stripe of light comprising points of light separated by known distances across the surface of the living tissue substantially in a first dimension;
wherein the light source moves the stripe of light across the surface of the living tissue substantially in a second dimension;
a camera that captures images of the strip of light at intervals synchronized with the moving of the stripe of light, and
wherein the processor further obtains the set of 3-dimensional coordinates based at least in part on, the known distances, the capturing of the images of the stripe of light at intervals synchronized with the moving of the stripe of light, and parallax between the camera and the light source.

* * * * *